US005866698A

United States Patent [19]

Ecker et al.

[11] Patent Number: 5,866,698

[45] Date of Patent: Feb. 2, 1999

[54] MODULATION OF GENE EXPRESSION THROUGH INTERFERENCE WITH RNA SECONDARY STRUCTURE

[75] Inventors: David Ecker, Carlsbad; Timothy A. Vickers, Vista; Thomas W. Bruice, Carlsbad, all of Calif.

[73] Assignee: Isis Pharmaceuticals, Inc., Carlsbad, Calif.

[21] Appl. No.: 227,180

[22] Filed: Apr. 13, 1994

Related U.S. Application Data

[63] Continuation of Ser. No. 801,168, Nov. 20, 1991, abandoned, which is a continuation-in-part of Ser. No. 518,929, May 4, 1990, abandoned, which is a continuation-in-part of Ser. No. 002,558, Apr. 15, 1991, abandoned.

[51] Int. Cl.$^6$ .......................... C07H 21/02; C07H 21/04

[52] U.S. Cl. .......................... 536/24.5; 536/23.1

[58] Field of Search .......................... 536/23.1, 24.1, 536/24.5; 435/5, 6

[56] References Cited

FOREIGN PATENT DOCUMENTS

| | | |
|---|---|---|
| 331939 | 9/1989 | European Pat. Off. . |
| 386563 | 9/1990 | European Pat. Off. . |
| WO91/04753 | 4/1991 | WIPO . |

OTHER PUBLICATIONS

Guro, "Antisense Has Growing Pains" Science, vol. 270, 27 Oct. 1995, pp. 575–577.

Lamond et al., "Probing the Structure and Function of U2 an RNP with Antisense Oligonucleotides Mode of 2'–OMeRNA", Cell, vol. 58, pp. 383–390. Jul. 28, 1989.

Vickers and Ecker, "Enhancement of Ribosomal Frameshifting by Oligonucleotides Targeted to the HIV gag pol Region" *Nucleic Acids Research* 20(15) :3945–3953 (1988).

Agrawal et al., "Oligodeoxynucleoside phosphoramidates and phosphorothioates as inhibitors of human immunodeficiency virus," *Proc. Nat'l. Acad. Sci. USA,* 85:7079 (1988).

Agrawal et al., "Inhibition of human immunodeficiency virus in early infected and chronically infected cells by antisense oligodeoxynucleotides and their phosphorothioate analogues," *Proc. Natl. Acad. Sci. USA*, 86:7790 (1989).

Arnott and Selsing, "Structures for the Polynucleotide Complexes Poly(dA)•Poly(dT) and Poly(dT)•Poly(dA)•–Poly(dT)," *J. Mol. Biol.,* 88:509 (1974).

Brierley et al., "Characterization of an Efficient Coronavirus Ribosomal Frameshifting Signal: Requirement for an RNA Pseudoknot," *Cell,* 57:537 (1989).

Broitman et al., "Formation of the triple–stranded polynucleotide helix, poly(A•A•U)," *Proc. Natl. Acad. Sci. USA,* 84:5120 (1987).

Casey et al., "Iron–Responsive Elements: Regulatory RNA Sequences That Control mRNA Levels and Translation," *Science,* 240:924 (1988).

Dayton et al., "Cis–Acting Sequences Responsive to the rev Gene Product of the Human Immunodeficiency Virus," *J. Acq. Immune Deficiency Syndromes,* 1:441 (1988).

Feng and Holland, "HIV–1 tat trans–activation requires the loop sequence within tar," *Nature,* 334:165 (1988).

Goodchild et al., "Inhibition of human immunodeficiency virus replication by antisense oligodeoxynucleotides," *Proc. Natl. Acad. Sci. USA,* 85:5507 (1988).

Hanvey et al., "Intramolecular DNA triplexes in supercoiled plasmids," *Proc. Natl. Acad. Sci. USA,* 85:6292 (1988).

Haseltine and Wong–Staal, *Scientific American,* 52 (Oct., 1988).

Jacks et al., "Two efficient ribosomal frameshifting events are required for synthesis of mouse mammary tumor virus gag–related polyproteins," *Proc. Natl. Acad. Sci. USA*, 84:4298 (1987).

Larson and Sells, "The function of proteins that interact with mRNA," *Mol. Cell. Biochem.,* 74:5 (1987).

Le et al., "Stability of RNA stem–loop structure and distribution of non–random structure in the human immunodeficiency virus (HIV–1)," *Nucl. Acids Res.,* 16:5153 (1988).

Letsinger et al., "Cholesteryl–conjugated oligonucleotides: Synthesis, properties, and activity as inhibitors of replication of human immunodeficiency virus in cell culture," *Proc. Natl. Acad. Sci. USA,* 86:6553 (1989).

Loose–Mitchell, "Antisense nucleic acids as a potential class of pharmaceutical agents," *TIPS,* vol. 9, pp. 45–47 (1988).

Marcus–Sekura, "Techniques for Using Antisense Oligodeoxyribonucleotides to Study Gene Expression," *Anal. Biochemistry,* vol. 172, 289–295 (1988).

Malter, "Identification of an AUUUA–Specific Messenger RNA Binding Protein," *Science,* 246:664 (1989).

Matsukura et al., "Phosphorothioate analogs of oligodeoxynucleotides: Inhibitors of replication and cytopathic effects of human immunodeficiency virus," *Proc. Natl. Acad. Sci. USA,* 84:7706 (1987).

Jaeger et al., "Improved predictions of secondary structures for RNA," *Proc. Natl. Acad. Sci. USA,* 86:7706 (1989).

Mori et al., "Phosphoroselenoate oligodeoxynucleotides: synthesis, physico–chemical characterization, anti–sense inhibitory properties and anti–HIV activity," *Nucleic Acids Res.,* 17:8207 (1989).

(List continued on next page.)

*Primary Examiner*—David Guzo
*Attorney, Agent, or Firm*—Law offices of Jane Massey Licata

[57] ABSTRACT

Methods for modulating the expression of viral genes are provided by selecting a portion of RNA coded by the gene, said RNA portion having subportions forming a secondary structure, and contacting the RNA with oligonucleotide of 6 to 50 which can bind with at least one of said subportions of the RNA. In accordance with the preferred embodiments, oligonucleotides are designed to bind to RNA secondary structures which are of significance to the expression of the gene coding for said RNA. In accordance with a preferred embodiment, methods of treatment of human immunodeficiency virus are similarly disclosed wherein the oligonucleotides are targeted at the CAR or gag-pol region of HIV RNA.

7 Claims, 7 Drawing Sheets

OTHER PUBLICATIONS

Ratner et al., "Complete nucleotide sequence of the AIDS virus, HTLV–III," *Nature,* 313:277 (1985).

Resnekov et al., "RNA Secondary Structure Is an Integral Part of the in vitro Mechanism of Attenuation in Simian Virus 40," *J. Biol. Chem.,* 264:9953 (1989).

Sarin et al., "Inhibition of acquired immunodeficiency syndrome virus by oligodeoxynucleoside methylphosphonates," *Proc. Natl. Acad. Sci. USA,* 85:7448 (1988).

Stein & Cohen, "Oligodeoxynucleotides as Inhibitors of Gene Expression: A Review," *Cancer Research,* 48:2659–2668 (1988).

Zaia et al., "Inhibition of Human Immunodeficiency Virus by Using an Oligonucleoside Methylphosphonate Targeted to the tat–3 Gene," *J. Virol.,* 62: 3914 (1988).

Zamecnik et al., "Inhibition of replication and expression of human T–cell lymphotropic virus type III in cultured cells by exogenous synthetic oligonucleotides complementary to viral RNA," *Proc. Natl. Acad. Sci. USA,* 83:4143 (1986).

Zon, "Synthesis of Backbone–Modified DNA Analogues for Biological Applications," *Journal of Protein Chemistry,* 6:131–145 (1987).

Zon, "Oligonucleotide Analogues as Potential Chemotherapeutic Agents," *Pharmaceutical Research,* 5:539–549 (1988).

Zuker, "On Finding All Suboptimal Foldings of an RNA Molecule," *Science,* 244:48 (1989).

Lamond, et al., "Probing the Structure and Function of U2 snRNP with Antisense Oligonucleotides Made of 2'–OMe RNA," *Cell,* 58:383–390 (1989).

Jacks et al, "Characterization of Ribosomal Frameshifting in HIV–1 'gag–pol' Expression", Nature, vol. 331, No. 21 pp. 280–283, 1988.

Dayton et al, "Functional Analysis of CAR, the Target Sequence for the Rev Protein of HIV–1", Science, vol. 246 pp. 1625–1629, Dec. 1989.

Shibahara et al., "Inhibition of human immunodeficiency virus (HIV–1) replication by synthetic oligo–RNA derivatives," *Nucl. Acids Res.,* 17:239 (1989).

Stevenson and Iversen, "Inhibition of Human Immunodeficiency Virus Type 1–mediated Cytopathic Effects by Poly (L–lysine)–conjugated Synthetic Oligodeoxyribonucleotides," *J. Gen. Virol.,* 70:2673 (1989).

Tinoco et al., "RNA Structure from A to Z," *Cold Spring Harb. Symp. Quant. Biol.,* 52:135 (1987).

Tuerk et al., "CUUCGG hairpins: Extraordinarily stable RNA secondary structures associated with various biochemical processes," *Proc. Natl. Acad. Sci. USA,* 85:1364 (1988).

Turner and Sugimoto, "RNA Structure Prediction," *Annu. Rev. Biophys. Chem.,* 17:167 (1988).

Van der Krol et al., "Modulation of Eukaryotic Gene Expression by Complementary RNA or DNA Sequences," *BioTechniques,* 6:958–973 (1988).

Walder, "Antisense DNA and RNA: progress and prospects," *Genes & Development,* 2:502–504 (1988).

[7357]

UCCUUGGGUU CUUGGGAGCA GCAGGAAGCA CUAUGGGCGC AGCGUCAAUG

ACGCUGACGG UACAGGCCAG ACAAUUAUUG UCUGGUAUAG UGCAGCAGCA

GAACAAUUUG CUGAGGGCUA UUGAGGCGCA ACAGCAUCUG UUGCAACUCA

CAGUCUGGGG CAUCAAGCAG CUCCAGGCAA GAAUCCUGGC UGUGGAAAGA

UACCUAAAGG AUCAACAGCU CCUAGGAUU UGGGGUUGCU CUGGAAAACU

CAUUUGCACC ACUGCUGUGC

SEQUENCE LISTING ( 1 ) GENERAL INFORMATION:

( i i i ) NUMBER OF SEQUENCES: 51

( 2 ) INFORMATION FOR SEQ ID NO: 1:

( i ) SEQUENCE CHARACTERISTICS:
( A ) LENGTH: 12
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 1:

C C U U C C C U U G T A 1 2

( 2 ) INFORMATION FOR SEQ ID NO: 2:

( i ) SEQUENCE CHARACTERISTICS:
( A ) LENGTH: 13
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 2:

A G A A A A U U C C C U G 1 3

( 2 ) INFORMATION FOR SEQ ID NO: 3:

( i ) SEQUENCE CHARACTERISTICS:
( A ) LENGTH: 13
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 3:

C C A G A U C U U C C C U 1 3

( 2 ) INFORMATION FOR SEQ ID NO: 4:

( i ) SEQUENCE CHARACTERISTICS:
( A ) LENGTH: 8
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 4:

A U C U U C C C 8

( 2 ) INFORMATION FOR SEQ ID NO: 5:

( i ) SEQUENCE CHARACTERISTICS:
( A ) LENGTH: 8
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 5:

-continued

U C U U C C C U 8

( 2 ) INFORMATION FOR SEQ ID NO: 6:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 6:

C A T G G T C C T C C T A C A G G G T C 2 0

( 2 ) INFORMATION FOR SEQ ID NO: 7:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 7:

C A U G G U C C U C C U A C A G G G U C 2 0

( 2 ) INFORMATION FOR SEQ ID NO: 8:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 8:

G A A A A U U C C U U U A U C U U C C C 2 0

( 2 ) INFORMATION FOR SEQ ID NO: 9:

( i ) SEQUENCE CHARACTERISTICS:
( A ) LENGTH: 23
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 9:

A G A A A A T T T C N N N T C T T C C C T A A 2 3

( 2 ) INFORMATION FOR SEQ ID NO: 10:

( i ) SEQUENCE CHARACTERISTICS:
( A ) LENGTH: 25
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 10:

A G A A A A T T T C N N N N N T C T T C C C T A A 2 5

( 2 ) INFORMATION FOR SEQ ID NO: 11:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 11:

C C C U U C C A N U C 1 1

( 2 ) INFORMATION FOR SEQ ID NO: 12:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 12:

C C C U U C C G N U C 1 1

( 2 ) INFORMATION FOR SEQ ID NO: 13:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 13:

C C C U U C C C N U C 1 1

( 2 ) INFORMATION FOR SEQ ID NO: 14:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 14:

C C C U U C C U N U C 1 1

( 2 ) INFORMATION FOR SEQ ID NO: 15:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 15:

C C C U U C C C A U C 1 1

( 2 ) INFORMATION FOR SEQ ID NO: 16:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 16:

C C C U U C C C G U C 1 1

( 2 ) INFORMATION FOR SEQ ID NO: 17:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 17:

C C C U U C C C C U C 1 1

( 2 ) INFORMATION FOR SEQ ID NO: 18:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 18:

C C C U U C C C U U C 1 1

( 2 ) INFORMATION FOR SEQ ID NO: 19:

( i ) SEQUENCE CHARACTERISTICS:
( A ) LENGTH: 17
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 19:

G C C C A T A G T G C T T C C T G 1 7

( 2 ) INFORMATION FOR SEQ ID NO: 20:

( i ) SEQUENCE CHARACTERISTICS:
( A ) LENGTH: 17
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 20:

T C A T T G A C G C T G C G C C C 1 7

( 2 ) INFORMATION FOR SEQ ID NO: 21:

( i ) SEQUENCE CHARACTERISTICS:
( A ) LENGTH: 17
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 21:

T A C C G T C A G C G T C A T T G 1 7

( 2 ) INFORMATION FOR SEQ ID NO: 22:

( i ) SEQUENCE CHARACTERISTICS:
( A ) LENGTH: 17
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 22:

T G T C T G G C C T   G T A C C G T   1 7

( 2 ) INFORMATION FOR SEQ ID NO: 23:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 23:

C C C U U C C N N U   C U A U C U U C C C   2 0

( 2 ) INFORMATION FOR SEQ ID NO: 24:

( i ) SEQUENCE CHARACTERISTICS:
( A ) LENGTH: 19
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 24:

C C C U U C C N N U   C A U C U U C C C   1 9

( 2 ) INFORMATION FOR SEQ ID NO: 25:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 25:

G T G C A A A T G A   G T T T T C C A G A   2 0

( 2 ) INFORMATION FOR SEQ ID NO: 26:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 26:

G C A A C C C C A A   A T C C C C A G G A   2 0

( 2 ) INFORMATION FOR SEQ ID NO: 27:

( i ) SEQUENCE CHARACTERISTICS:
( A ) LENGTH: 20

-continued ( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 27:

G C T G T T G A T C   C T T T A G G T A T   2 0

( 2 ) INFORMATION FOR SEQ ID NO: 28:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 28:

C T T T C C A C A G   C C A G G A T T C T   2 0

( 2 ) INFORMATION FOR SEQ ID NO: 29:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 29:

T G C C T G G A G C   T G C T T G A T G C   2 0

( 2 ) INFORMATION FOR SEQ ID NO: 30:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 30:

C C C A G A C T G T   G A G T T G C A A C   2 0

( 2 ) INFORMATION FOR SEQ ID NO: 31:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 31:

A G A T G C T G T T   G C G C C T C A A T   2 0

( 2 ) INFORMATION FOR SEQ ID NO: 32:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes -continued ( x i ) SEQUENCE DESCRIPTION: SEQ ID NO: 32:

AGCCCTCAGC AAATTGTTCT 20

( 2 ) INFORMATION FOR SEQ ID NO: 33:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 33:

GCTGCTGCAC TATACCAGAC 20

( 2 ) INFORMATION FOR SEQ ID NO: 34:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 34:

AATAATTGTC TGGCCTGTAC 20

( 2 ) INFORMATION FOR SEQ ID NO: 35:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 35:

CGTCAGCGTC ATTGACGCTG 20

( 2 ) INFORMATION FOR SEQ ID NO: 36:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 36:

CGCCCATAGT GCTTCCTGCT 20

( 2 ) INFORMATION FOR SEQ ID NO: 37:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 37:

GCTCCCAAGA ACCCAAGGAA 20

( 2 ) INFORMATION FOR SEQ ID NO: 38:

( i ) SEQUENCE CHARACTERISTICS:
( A ) LENGTH: 21
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 38:

TAGGAAGGCC AGATCTTCCC T 21

( 2 ) INFORMATION FOR SEQ ID NO: 39:

( i ) SEQUENCE CHARACTERISTICS:
( A ) LENGTH: 37
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 39:

AAGAAAATTC CCTGGCCTTC CCTTGTAGGA AGGCCAG 37

( 2 ) INFORMATION FOR SEQ ID NO: 40:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 40:

TGCTCTGAAG AAAATTCCCT 20

( 2 ) INFORMATION FOR SEQ ID NO: 41:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 41:

TCTGAAGAAA ATTCCCTGGC 20

( 2 ) INFORMATION FOR SEQ ID NO: 42:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 42:

GAAGAAAATT CCCTGGCCTT 20

( 2 ) INFORMATION FOR SEQ ID NO: 43:

( i ) SEQUENCE CHARACTERISTICS:
( A ) LENGTH: 20

( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 43:

C T G G C C T T C C   C T T G T A G G A A   2 0

( 2 ) INFORMATION FOR SEQ ID NO: 44:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 44:

G C C T T C C C T T   G T A G G A A G G C   2 0

( 2 ) INFORMATION FOR SEQ ID NO: 45:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 45:

T T C C C T T G T A   G G A A G G C C A G   2 0

( 2 ) INFORMATION FOR SEQ ID NO: 46:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 46:

C C T T G T A G G A   A G G C C A G A T C   2 0

( 2 ) INFORMATION FOR SEQ ID NO: 47:

( i ) SEQUENCE CHARACTERISTICS:
( A ) LENGTH: 20
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 47:

T G T A G G A A G G   C C A G A T C T T C   2 0

( 2 ) INFORMATION FOR SEQ ID NO: 48:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes -continued ( x i ) SEQUENCE DESCRIPTION: SEQ ID NO: 48:

C C C T T C C N N T T 11

( 2 ) INFORMATION FOR SEQ ID NO: 49:

( i ) SEQUENCE CHARACTERISTICS:
( A ) LENGTH: 9
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 49:

C C T T C C N N T 9

( 2 ) INFORMATION FOR SEQ ID NO: 50:

( i ) SEQUENCE CHARACTERISTICS:
( A ) LENGTH: 11
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 50:

G G G A A G G N N A G 11

( 2 ) INFORMATION FOR SEQ ID NO: 51:

( i ) SEQUENCE CHARACTERISTICS:
( A ) LENGTH: 9
( B ) TYPE: nucleic acid
( C ) STRANDEDNESS: single
( D ) TOPOLOGY: linear ( i v ) ANTI-SENSE: yes ( x i ) SEQUENCE DESCRIPTION: SEQ ID NO: 51:

G G A A G G N N A 9

MODULATION OF GENE EXPRESSION THROUGH INTERFERENCE WITH RNA SECONDARY STRUCTURE

INTRODUCTION

This is a continuation, of application Ser. No. 07/801,168, filed Nov. 20, 1991, now abandoned, which is a continuation in part of Ser. No. 518,929, filed May 4, 1990, abandoned , which is CIP of Ser. No. 01/002,558 filed Apr. 15, 1991 and Ser. No. PCT/US91/02558, filed Apr. 15, 1991 abandoned.

FIELD OF THE INVENTION

This invention relates to the field of therapeutics, particularly the treatment of infections caused by viruses and retroviruses, such as the human immunodeficiency virus (HIV). It relates to the design, synthesis and application of oligonucleotides which inhibit the activity of retroviruses and other viruses.

BACKGROUND OF THE INVENTION

This invention relates to materials and methods for modulating the activity of viral RNA. The invention generally relates to the field of "antisense" compounds, compounds which are capable of specific hybridization with a nucleotide sequence of an RNA. In accordance with preferred embodiments, this invention is directed to methods for achieving therapeutic treatment of disease and regulating gene activity.

It is well known that most of the bodily states in mammals including infectious disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. By interfering with the production of proteins, it has been hoped to effect therapeutic results with maximum effect and minimal side effects. It is the general object of such therapeutic approaches to interfere with or otherwise modulate gene expression leading to undesired protein formation.

One method for inhibiting specific gene expression which has been adopted to some degree is the "antisense" approach, where oligonucleotide analogs complementary to a specific target messenger RNA (mRNA) sequence are used. A number of workers have reported such attempts. Pertinent reviews include C. A. Stein & J. S. Cohen, *Cancer Research*, vol. 48, pp. 2659–2668 (1988); J. Walder, *Genes & Development*, vol. 2, pp. 502–504 (1988); C. J. Marcus-Sekura, *Anal. Biochemistry*, vol. 172, 289–295 (1988); G. Zon, *Journal of Protein Chemistry*, vol. 6, pp-131–145 (1987); G. Zon, *Pharmaceutical Research*, vol. 5, pp. 539–549 (1988); A. R. Van der Krol, J. N. Mol, & A. R. Stuitje, *BioTechniques*, vol. 6, pp. 958–973 (1988) and D. S. Loose-Mitchell, *TIPS*, vol. 9, pp. 45–47 (1988). Each of the foregoing provide background concerning general antisense theory and prior techniques.

Prior attempts to inhibit HIV by various antisense approaches have been made by a number of researchers. Zamecnik and coworkers have used phosphodiester oligonucleotides targeted to the reverse transcriptase primer site and to splice donor/acceptor sites, P. C. Zamecnik, J. Goodchild, Y. Taguchi, P. S. Sarin, *Proc. Natl. Acad. Sci. USA*, 83:4143 (1986). Goodchild and coworkers have made phosphodiester compounds targeted to the initiation sites for translation, the cap site, the polyadenylation signal, the 5' repeat region and a site between the gag and pol genes. J. Goodchild, S. Agrawal, M. P. Civeira, P. S. Sarin, D. Sun, P.C. Zamecnik, *Proc. Natl. Acad. Sci. USA*, 85:5507 (1988). In the Goodchild study, the greatest activity was achieved by targeting the polyadenylation signal. Agrawal and coworkers have extended the studies of Goodchild by using chemically modified oligonucleotide analogs which were also targeted to the cap and splice donor/acceptor sites. S. Agrawal, J. Goodchild, M. P. Civeira, A. H. Thornton, P. S. Sarin, P. C. Zamecnik, *Proc. Nat'l. Acad. Sci. USA*, 85:7079 (1988). A portion of one of these overlapped a portion of the HIV TAR region but was not found to have exemplary effect. Neither was this oligonucleotide analog designed to interfere with the HIV TAR region. Agrawal and coworkers have used oligonucleotide analogs targeted to the splice donor/acceptor site to inhibit HIV infection in early infected and chronically infected cells. S. Agrawal, T. Ikeuchi, D. Sun, P. S. Sarin, A. Konopka, J. Maizel, *Proc. Natl. Acad. Sci. USA*, 86:7790 (1989).

Sarin and coworkers have also used chemically modified oligonucleotide analogs targeted to the cap and splice donor/acceptor sites. P. S. Sarin, S. Agrawal, M. P. Civeira, J. Goodchild, T. Ikeuchi, P. C. Zamecnik, *Proc. Natl. Acad. Sci. USA*, 85:7448 (1988). Zaia and coworkers have also used an oligonucleotide analog targeted to a splice acceptor site to inhibit HIV. J. A. Zaia, J. J. Rossi, G. J. Murakawa, P. A. Spallone, D. A. Stephens, B. E. Kaplan, *J. Virol.*, 62: 3914 (1988). Matsukura and coworkers have synthesized oligonucleotide analogs targeted to the initiation of translation of the rev gene mRNA. M. Matsukura, K. Shinozuka, G. Zon, et al., *Proc. Natl. Acad. Sci. USA*, 84:7706 (1987); R. L. Letsinger, G. R. Zhang, D. K. Sun, T. Ikeuchi, P. S. Sarin, *Proc. Natl. Acad. Sci. USA*, 86:6553 (1989). Mori and coworkers have used a different oligonucleotide analog targeted to the same region as Matsukura. K. Mori, C. Boiziau, C. Cazenave, et al., *Nucleic Acids Res.*, 17:8207 (1989). Shibahara and coworkers have used oligonucleotide analogs targeted to a splice acceptor site as well as the reverse transcriptase primer binding site. S. Shibahara, S. Mukai, H. Morisawa, H. Nakashima, S. Kobayashi, N. Yamamoto, *Nucl. Acids Res.*, 17:239 (1989). Letsinger and coworkers have synthesized and tested oligonucleotide analogs with conjugated cholesterol targeted to a splice site. K. Mori, C. Boiziau, C. Cazenave, et al., *Nucleic Acids Res.*, 17:8207 (1989). Stevenson and Iversen have conjugated polylysine to oligonucleotide analogs targeted to the splice donor and the 5'-end of the first exon of the tat gene. M. Stevenson, P. L. Iversen, *J. Gen. Virol.*, 70:2673 (1989).

These prior attempts at targeting HIV have largely focused on the nature of the chemical modification used in the oligonucleotide. Although each of the above publications have reported some degree of success in inhibiting some function of the virus, a general therapeutic scheme to target HIV and other viruses has not been found. Accordingly, there has been and continues to be a long-felt need for the design of oligonucleotides which are capable of effective, therapeutic antisense use.

This long-felt need has not been satisfied by prior work in the field of antisense oligonucleotide therapy for HIV and other retroviruses and viruses. Others have failed to identify target sites in which antisense oligonucleotides or oligonucleotide analogs are therapeutically effective at reasonable rates of application.

OBJECTS OF THE INVENTION

It is a principal object of the invention to provide therapies for human diseases, particularly the human immunodeficiency virus and other human retroviruses.

It is a further object of the invention to provide molecules, especially oligonucleotides, which perturb the structure of mRNA.

Yet another object of this invention is to modulate gene expression in cells.

A further object is to interfere with the secondary structure of RNAs through interaction of those structures with oligonucleotides.

Another object is to effect such interference through formation of perturbed RNA secondary structures.

Another object is to effect such interference through formation of nucleotide triplexes.

These and other objects of this invention will become apparent from a review of the instant specification.

SUMMARY OF THE INVENTION

A new paradigm for targeting antisense oligonucleotides to HIV and other retroviruses, viruses and other infectious agents has now been discovered. Prior attempts at antisense targeting to HIV have been focused on inhibition of the synthesis of some particular viral protein thought to be essential to the success of the infection. In the present invention, the same goal (inhibition of viral gene expression) is achieved, but greater, therapeutically significant activity is obtained by targeting particular sites on the HIV or other virus RNA. In the present invention, target RNA structures which have important biological function have been found to be the key target sites. They are interfered with at the level of those structures. It has been determined that targeting these RNA structures is a key to effective antisense therapy with oligonucleotides.

In accordance with the present invention, methods of modulating the expression of genes are provided. These comprise selecting or identifying a portion of RNA coded by the gene which has subportions forming a secondary structure. The RNA, or cells containing it, is then contacted with oligonucleotide which can bind with at least one of the subportions of the RNA. It is preferred that the oligonucleotide be designed so as to be capable of disrupting the secondary structure of the RNA to effect the inhibition of expression of a gene. The gene is generally one which is believed to give rise to a disease state in an organism and is typically a virus or retrovirus although other infectious organisms can be so attacked.

It is preferred that the oligonucleotide be capable of binding with at least about six nucleotides of the RNA subportion. It is more preferred that from eight to fifty nucleotides be capable of being bound, with from about 10 to about 20 nucleotides being even more preferred.

In accordance with preferred embodiments, the oligonucleotide is capable of forming a duplex structure with the subportion of RNA. Alternatively, and in accordance with certain preferred embodiments, the oligonucleotide can form a triplex structure with the selected portion of RNA. While the mechanism of the interaction is not known with certainty, it is possible that it may effect modulation of gene expression through a number of ways.

In accordance with preferred embodiments, the RNA portion which is interfered with comprises at least a part of the TAR element of HIV. Other preferred embodiments lead to the interaction of oligonucleotides with the CAR element of HIV or with the gag-pol region of HIV RNA.

The oligonucleotides in accordance with this invention are themselves believed to be novel. Thus, oligonucleotides which are capable of interacting with subportions of RNA which are capable of forming secondary structures are comprehended. It is also intended that methods of treating animals suspected of having a disease characterized by expression of a gene coding for RNA having a secondary structure may also be provided. Thus, animals suspected of having the disease are contacted with oligonucleotides which can bind with the secondary structure of the RNA implicated in the disease process. In particular, the present invention is believed to be effective in the treatment of retroviral and other viral infections in mammals, especially man. Thus, oligonucleotides designed to interact with the TAR, CAR or gag-pol regions of HIV RNA are administered to animals, especially humans suspected of being infected with human immunodeficiency virus.

A host of other viral, retroviral, and other infectious diseases are believed to be amenable to therapeutics in accordance with the present invention.

BRIEF DESCRIPTION OF THE DRAWINGS

FIG. 1 sets forth the partial linear structure of the HIV-1 CAR RNA sequence corresponding to nucleotides 7357–7627.

DETAILED DESCRIPTION OF PREFERRED EMBODIMENTS

Figure 2:
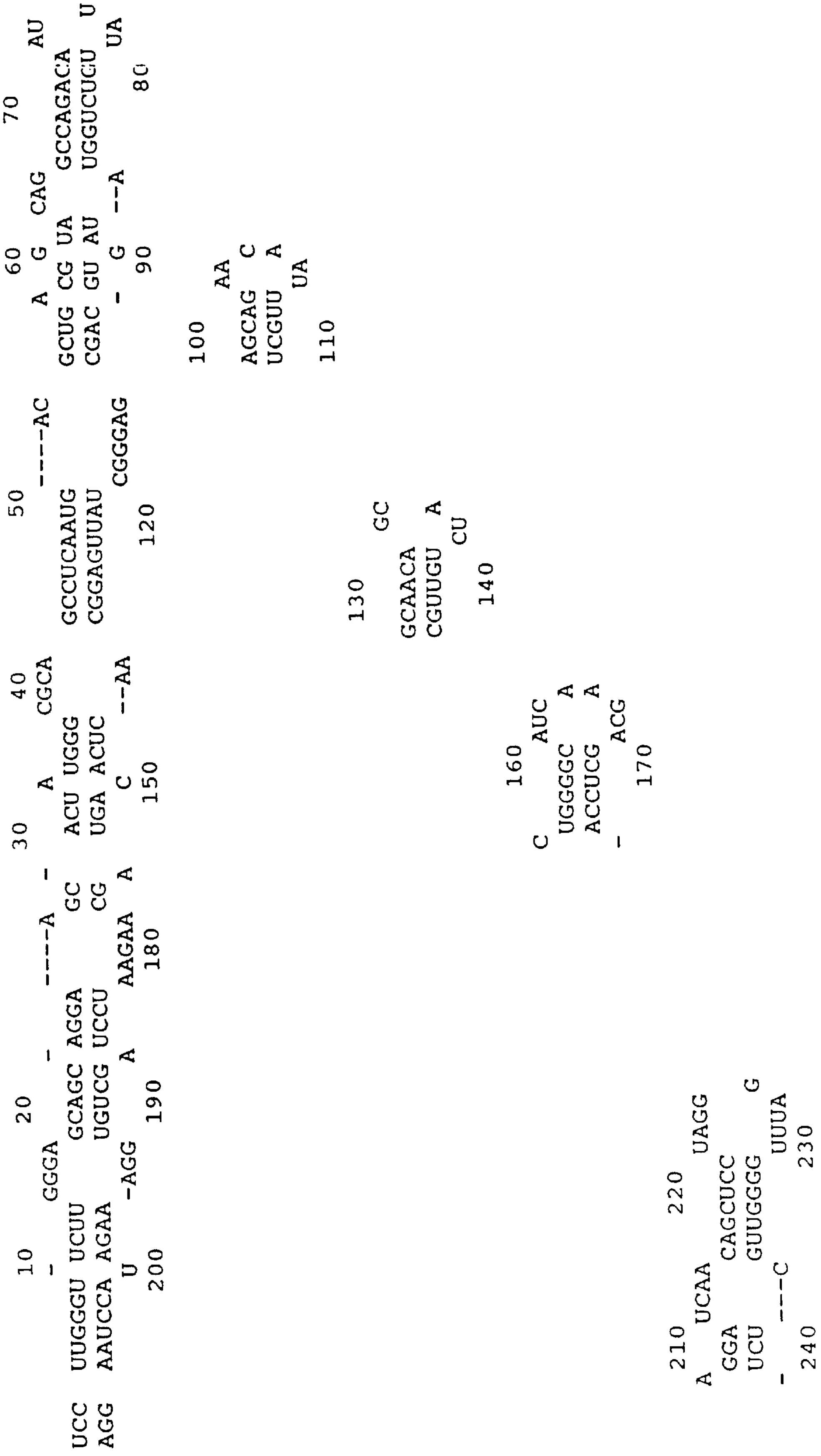
FIG. 2 shows a computer-predicted secondary structure of the HIV-1 CAR element.

The biological function of RNA is mediated by its structure. mRNA is generally thought of as a linear molecule which contains the information for directing protein synthesis within the sequence of ribonucleotides. Recently, studies have revealed a number of secondary and tertiary structures in mRNA which are important for its function. I. Tinoco, Jr. P. W. Davis, C. C. Hardin, J. D. Puglisi, G. T. Walker, *Cold Spring Harb. Symp. Quant. Biol.*, 52:135 (1987). Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure.

Very little is known about the precise three dimensional structure of RNA. However, there have recently been a number of research efforts which have shown that RNA structures, including single stranded, secondary and tertiary structures, have important biological functions beyond simply encoding the information to make proteins in linear sequences. Some of these correlations have been discussed in the following publications: I. Tinoco, Jr., P. W. Davis, C. C. Hardin, J. D. Puglisi, G. T. Walker, *Cold Spring Harb. Symp. Quant. Biol.*, 52:135 (1987); O. Resnekov, M. Kessler, Y. Aloni, *J. Biol. Chem.*, 264:9953 (1989); C. Tuerk, P. Gauss, C. Thermes, et al., *Proc. Natl. Acad. Sci. USA*, 85: 1364 (1988); and D. E. Larson, B. H. Sells, *Mol. Cell. Biochem.*, 74:5 (1987). Despite the fact that there is little precise structural information on RNA, a number of researchers have measured the binding energies of a large number of RNA duplex structures and have derived a set of rules which can be used to predict the secondary structure of RNA. J. A. Jaeger, D. H. Turner, M. Zuker, *Proc. Natl. Acad. Sci. USA*, 86:7706 (1989); D. H. Turner, N. Sugimoto, *Annu. Rev. Biophys. Biophys. Chem.*, 17:167 (1988). In conjunction with experimental data, these rules are useful in identification of RNA structural elements with important biological function.

It has been discovered to be possible to regulate the activity of RNA in cells by introducing oligonucleotides which perturb or interfere with the secondary structure of natural RNA. The oligonucleotides interfere with the normal interaction between the RNA and the factors that bind to it. This method can be used to treat diseases, particularly HIV and other retroviruses. In accordance with the present invention, compositions which bind to biological RNA molecules with significant structural features of biological importance are provided. The present invention employs oligonucleotides which bind to these structures. In the context of this invention, the term "oligonucleotide" refers to a plurality of joined nucleotide units formed from naturally occurring bases and pentofuranosyl groups joined by native phosphodiester bonds. This term effectively refers to naturally occurring species or their close homologs.

"Oligonucleotide" may also refer to moieties which function similarly to oligonucleotides but which have non-naturally occurring portions. Thus, oligonucleotides may have altered sugar moieties or inter-sugar linkages. Exemplary among these are the phosphorothioate and other sulfur containing species which are known for use in the art. They may also comprise altered base units or other modifications consistent with the spirit of this invention.

In accordance with certain preferred embodiments, at least some of the phosphodiester bonds of the oligonucleotide have been substituted with a structure which functions to enhance the ability of the compositions to penetrate into the region of cells where the RNA whose activity is to be modulated is located. It is preferred that such linkages be sulfur-containing. It is presently preferred that such substitutions comprise phosphorothioate bonds. Others such as alkyl phosphothioate bonds, N-alkyl phosphoramidates, phosphorodithioates, alkyl phosphonates, and short chain alkyl or cycloalkyl structures may also be useful. In accordance with other preferred embodiments, the phosphodiester bonds are substituted with structures which are, at once, substantially non-ionic and non-chiral. Persons of ordinary skill in the art will be able to select other linkages for use in the practice of the invention.

Oligonucleotides may also include species which include at least some modified base forms. Thus, purines and pyrimidines other than those normally found in nature may be so employed. Similarly, modifications on the pentofuranose portions of the nucleotides may also occur as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_nNH_2$ or $O(CH_2)_nCH_3$ where n is from 1 to about 20, and other substituents having similar properties.

Such oligonucleotides are best described as being functionally interchangeable with natural oligonucleotides (or synthesized oligonucleotides along natural lines), but which have one or more differences from natural structure. All such oligonucleotides are comprehended by this invention so long as they function effectively to bind to selected portions of RNA having secondary structure of functional significance.

The oligonucleotides in accordance with this invention preferably comprise from about 6 to about 50 nucleotides with from about 8 to about 30 nucleotides being more preferred, and still more preferred to have from about 10 to about 20 nucleotides. As will be appreciated, a nucleotide is a base and sugar combination suitably bound to adjacent nucleotides through phosphodiester or other bonds.

The oligonucleotides of this invention can be used in diagnostics, therapeutics and as research reagents and kits. For therapeutic use, the oligonucleotide is administered to an animal, especially a human, such as are suffering from a virus or retrovirus infection such as AIDS.

Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including opthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

It is generally preferred to apply the therapeutic agent in accordance with this invention internally such as orally, intravenously or intramuscularly. Other forms of administration, such as transdermally, topically or intralesionally may also be useful. Inclusion in suppositories may also be useful. Use of the oligonucleotides of this invention in prophylaxis is also likely to be useful. Use of pharmacologically acceptable carriers is also preferred for some embodiments. In accordance with the present invention, the oligonucleotides which are useful in its performance are best described by the RNA whose secondary structure is to interfered with. Thus, it will be understood by persons of ordinary skill in the art that the oligonucleotides provided by this invention are those which are capable of binding with RNA having a secondary structure bearing a causal or mediative relationship to a diseased state. All such oligonucleotides are comprehended by this invention so long as they bind the target RNA structure at or adjacent to a secondary structure thereof.

A number of RNA secondary structures have recently been identified for which application of this invention will likely provide therapeutic utility. Others will also be useful as well. Some of these include the HIV TAR structures; S. Feng, E. C. Holland, *Nature*, 334:165 (1988), including the stem loops at nucleotide 1–59, and 60–104 according to the nucleotide sequence as described by Ratner, L. Ratner L.; W. Haseltine, R. Patarca, K. J. Livak, B. Starcich, S. F. Josephs, *Nature*, 313:277 (1985); the boundary between the EGP/OMP regions of HIV, S. Le, J. Chen, M. J. Braun, M. A. Gonda, J. V. Maizel, *Nucl. Acids Res.*, 16:5153 (1988); the boundary between the TMP/env genes of HIV, S. Le, J. Chen, M. J. Braun, M. A. Gonda, J. V. Maizel, *Nucl. Acids Res.*, 16: 5153 (1988); the HIV CAR structure, E. T. Dayton, D. M. Powell, A. I. Dayton, *Science*, 246:1625 (1989); the stem loop structure at the junction between the HIV gag and pol genes (nucleotides 1629–1674); the HIV CRS element; and the human iron responsive element (IRE) J. L. Casey, M. W. Hentze, D. M. Koeller, et al., *Science*, 240:924 (1988).

In addition, there are regions of RNA which are primarily thought of as single stranded areas which have been identified as sites for protein binding. For example, the sequence 5'-AUUUA-3' has been identified as a signal for a protein to bind which leads to degradation of RNA. J. S. Malter, *Science*, 246:664 (1989). The structure of this region in not known. However, that does not preclude the practice of this invention with this sequence. Additional RNA elements, with as yet unknown structures, can also be the subject of this invention.

It is not absolutely necessary to know the actual RNA structure in order to practice this invention, it is only necessary to know that a specific RNA sequence is recognized by an RNA binding element and that this interaction has important biological consequences. In this regard, the viral RNA sequences and structures which are recognized by the structural proteins of retroviruses for virion formation may be the subject of this invention as may many others. It is not intended that application of this invention be limited to presently known structures. Binding to any RNA structure which has an important biological function falls within the spirit and scope of this invention.

This disclosure provides several methods to interfere with the natural function of an RNA structural element and others will be apparent to persons skilled in the art. By using the rules of Watson-Crick hybridization and free energy predictions for hybridization of oligonucleotides designed to be complementary to RNA which comprises secondary structures it has now been found that the oligonucleotides will compete with internal RNA structures by forming stable heteroduplexes. The energy barriers to heteroduplex formation are overcome by designing oligonucleotides to form a more stable heteroduplex than the internal RNA structure on the target RNA.

Kinetic considerations for strand invasion of an existing RNA duplex also enter into the oligonucleotide design. It is possible to disrupt an existing RNA secondary structure with an invading strand by designing the invading strand to have at least three, and preferably more bases complementary to regions to the target RNA which are not involved in base pairing. This provides a kinetic "foothold" for the invading strand to initiate the process of heteroduplex formation.

It is also disclosed that duplex RNA structure can be perturbed by binding to it by triple strand formation. In contrast to heteroduplex formation, where the RNA secondary structure is broken by an invading strand, triple strand formation generally preserves the existing RNA duplex hydrogen bonding pattern, but binds in a helical groove with additional hydrogen bonds. Triple strand formation is a phenomenon which has been known in a limited sense for some time. General reviews which describe triple strand formation with duplex DNA include; J. C Hanvey, M. Shimizu, R. D. Wells, *Proc. Natl. Acad. Sci. USA*, 85:6292 (1988); and S. Arnott, E. Selsing, *J. Mol. Biol.*, 88:509 (1974). Triple strand formation with RNA homopolymers has been previously described in S. L. Broitman, D. D. Im, J. R. Fresco, *Proc. Natl. Acad. Sci. USA*, 84:5120 (1987). It has not, however, previously been disclosed to inhibit the function of RNA by binding to duplex regions with oligonucleotides by triple strand formation. It is now believed, however, that binding to regions of RNA secondary structure, such as in the stem regions of stem-loops, will perturb the interactions between the natural RNA and the factors which bind to it, thus modulating gene expression.

In accordance with the present invention, it will be understood that the term "to bind" as it refers to the interaction between an oligonucleotide and an RNA portion or subportion may have any of several, related meanings. Thus, the present invention comprehends binding of an oligonucleotide with at least one of subportions forming a secondary structure of an RNA portion comprising them. It will be understood that the oligonucleotide will bind with at least one of the subportions of the RNA portion in a Watson-Crick fashion so as to form, locally, a heteroduplex between the RNA subportion and the oligonucleotide. This heteroduplex formation is believed to result in alteration of the secondary structure of the RNA portion. The exact mechanism and the result of this effect is not known with certainty, yet it is believed that the normal secondary structure of the RNA portion is gradually replaced by the binding of the oligonucleotide with one or more of the subportions of the RNA portion. Since the electronic and steric factors which attend the new heteroduplex are different from those of the naturally occurring RNA portion, the effectiveness and nature of the function to generate protein from the RNA is interfered with. The resulting formation of defective or missing protein manifests itself overall as a modulation in the expression of the gene coding for the RNA.

The present invention also comprehends the formation of triplexes with RNA portions having secondary structures. Once again, the precise nature of such triplexes is not fully understood however it is believed that suitably-constructed oligonucleotides can so interact with portions of RNA having a secondary structure in some circumstances. The resulting triplex formation is believed to grossly interfere with translation of protein from the RNA thus leading to modulation of expression of the gene from which the RNA derives.

In accordance with the invention it is not necessary that the interaction of oligonucleotide with the RNA portion or subportion—the binding of the two—result in either non-formation or malformation of protein. It may be in some circumstances that interruption of some control or other function having a significant role in the gene expression protocol may be an effective means of modulating that expression. One example of this relates to the gag-pol locus in HIV. Thus, it is not necessary that protein translation be stopped or that defective proteins be produced. Rather, through interference of the gag-pol region, it is believed possible to interfere with frame-shifting, which is believed to lead to the preparation of fusion proteins of significant importance to the HIV organism.

In short, any interaction or binding of oligonucleotide with an RNA having a secondary structure is believed to have the potential for interference with RNA function and, hence, for modulation of the expression of the gene from which the RNA derives. It is likely that persons of ordinary skill in the art will find other means of interfering with RNA secondary structures other than those set forth with specificity herein. All such means are, however, contemplated by the present invention.

While a wide variety of oligonucleotides are believed to be useful in practice of the present invention, it has been found to be preferred to design such oligonucleotides so as to bind with at least about six nucleotides of a subportion of an RNA portion having a secondary structure. In accordance with other preferred embodiments, oligonucleotides which combine with from about six to about 30 and even more preferably with about 10 to about 20 nucleotides are preferred. As discussed above, it is presently believed that the TAR element of HIV is an excellent target for employment of the present invention. Accordingly, preparations of oligonucleotides for binding with one or more subportions of the TAR region of HIV are preferred. A similar consideration attends the interference with the functioning of the CAR element of HIV. Accordingly, preparation of oligonucleotides which interfere with that portion are also preferred.

In a similar fashion, interference with gag-pol region of HIV RNA may also be preferred in accordance with the practice of certain embodiments of this invention. In such case, it is expected that frame-shifting will be interfered with leading to the malformation or non-formation of essential proteins of the gag-pol family.

Therapeutics are particular objects of the present invention. Thus, presenting oligonucleotides in accordance with the present invention in pharmaceutically acceptable carriers may be highly useful. It is desired to treat animals suspected of having diseases characterized by expression of genes coding for RNA having secondary structures. Thus, animals suspected of having such diseases are contacted with oligonucleotides which are designed to bind with a secondary structure of those RNAs. This is especially true for treatment of the disease AIDS. In such case, it is presently preferred to employ oligonucleotides which are targeted at the TAR, CAR or gag-pol regions of HIV RNA. Overall, it is preferred to administer to patients suspected of suffering from the foregoing disease states with amounts of oligonucleotide in either native form or suspended in a carrier medium in amounts and upon treatment schedules which are effective to reduce the symptomology of that disease. It is within the scale of a person's skill in the art to determine optimum dosages and treatment schedules for such treatment regimens.

EXAMPLES

Example 1. The HIV CAR element

One of the regulatory events in the life cycle of the human immunodeficiency virus is accumulation of the large virion structural RNA's which are accumulated at the expense of the shorter regulatory mRNA's. In essence, the virus uses much of the same RNA material to encode each set of proteins. If the RNA's are more extensively spliced, the regulatory proteins are produced. If the RNA's are less extensively spliced, the structural proteins are produced. W. A. Haseltine, F. Wong-Staal, *Scientific American*, 52 (October, 1988). These events are regulated by a protein known as rev, which a product of the rev gene. Rev's function is to enhance the transport of RNA from the nucleus of the cell to the cytoplasm. In the absence of rev, the mRNA's stay in the nucleus of the cell, where they are subject to splicing enzymes which convert them to mRNA's which encode regulatory proteins. In the presence of rev, the mRNA's are transported to the cytoplasm with less splicing. The resulting longer mRNA's encode structural proteins.

Rev functions by binding to an RNA structural element known as the CAR element. E. T. Dayton, D. M. Powell, A. I. Dayton, *Science*, 246:1625 (1989). This structural element has also been referred to as the rre (rev-responsive element). The functional RNA has been localized to a 269 bp region in the env RNA with the coordinates 7358–7627. L. Ratner, W. Haseltine, R. Patarca, K. J. Livak, B. Starcich, S. F. Josephs, *Nature*, 313:277 (1985). The sequence is shown in FIG. 1. For convenience, this structure is referred to as the CAR element. The secondary structure of the CAR element is currently not known with certainty. However, it is possible to predict the secondary structure of the CAR element using computer programs commonly used by those skilled in the art such as the program of Zuker. M. Zuker, *Science*, 244:48 (1989). The result of such an analysis yields the result shown in FIG. 2. Each of the stem loop structures shown in FIG. 2 have the potential to interact with the rev gene product and each can be bound by oligonucleotides as part of this invention. It is by no means certain that the structures predicted by the computer program and illustrated in FIG. 2 are correct or exhaustive. This does not restrict the practice of this invention for the CAR element structure, however. In this and all other cases where the actual RNA structure is uncertain, the invention can be practiced by preparing a series of oligonucleotides which are complementary to the sequence, where the oligonucleotides are designed with the constraints and with the considerations set forth herein.

Assays to measure the normal function of the rev gene product can be performed according to published procedures. E. T. Dayton, D. M. Powell, A. I. Dayton, *Science*, 246:1625 (1989); Dayton et al., *J. Acq. Immune Deficiency Syndromes*, 1:441 (1988). Vectors which express HIV mRNA in cells under regulatory control of a variety of promoters are transfected into cells along with a vector which expresses the rev protein. When rev functions normally to facilitate the transport of mRNA to the cytoplasm, the transported mRNA's encode the gag protein, which is detected by an immunoabsorbant assay. When oligonucleotides interfere with this process, a decrease in the production of gag protein is measured. The reagents needed to conduct these experiments are available from the National Institutes of Health, *Aids Research and Reference Reagent Program*, 1990 catalog, National Institute of Allergy and Infectious Diseases.

The effects of oligonucleotides will be determined by adding the compounds directly to the transfection mixture or by adding the compounds to the media at various times and concentrations following transfection, followed by the assay at 24–48 hours post-transfection.

The following oligonucleotides will be studied.

| Sequence 5'--3' |
| --- |
| GTGCAAATGAGTTTTCCAGA (SEQ ID NO: 25) |
| GCAACCCCAAATCCCCAGGA (SEQ ID NO: 26) |
| GCTGTTGATCCTTTAGGTAT (SEQ ID NO: 27) |
| CTTTCCACAGCCAGGATTCT (SEQ ID NO: 28) |
| TGCCTGGAGCTGCTTGATGC (SEQ ID NO: 29) |
| CCCAGACTGTGAGTTGCAAC (SEQ ID NO: 30) |
| AGATGCTGTTGCGCCTCAAT (SEQ ID NO: 31) |
| AGCCCTCAGCAAATTGTTCT (SEQ ID NO: 32) |
| GCTGCTGCACTATACCAGAC (SEQ ID NO: 33) |
| AATAATTGTCTGGCCTGTAC (SEQ ID NO: 34) |
| CGTCAGCGTCATTGACGCTG (SEQ ID NO: 35) |
| CGCCCATAGTGCTTCCTGCT (SEQ ID NO: 36) |
| GCTCCCAAGAACCCAAGGAA (SEQ ID NO: 37) |

Example 2. Inhibition of Frame Shifting: the HIV gag/pol Frameshift Region.

HIV and other retroviruses synthesize a protein which encodes a reverse transcriptase, pol, as part of a fusion with a structural protein known as gag. The virus also encodes a sequence-specific protease which cleaves between the gag and pol domains of the fusion protein to release free pol. In all retroviruses examined to date, the genetic sequence of the gag-pol mRNA precludes direct translation of the mRNA into a gag-pol fusion protein. Either there is an in-frame termination codon between the gag and pol domains on the mRNA, or the gag and pol sequences are not in the same reading frame of the message. T. Jacks, M. D. Power, F. R. Masiarz, P. A. Luciw, P. J. Barr, H. E. Varmus, *Nature*, 331:280 (1988). In the case of HIV, the pol reading frame is −1 relative to gag. In order to express a fusion protein the ribosome “frame shifts” at the junction between the gag and pol regions on the mRNA and continues translation in the reading frame of pol until completion of synthesis of the fusion protein.

Figure 3:
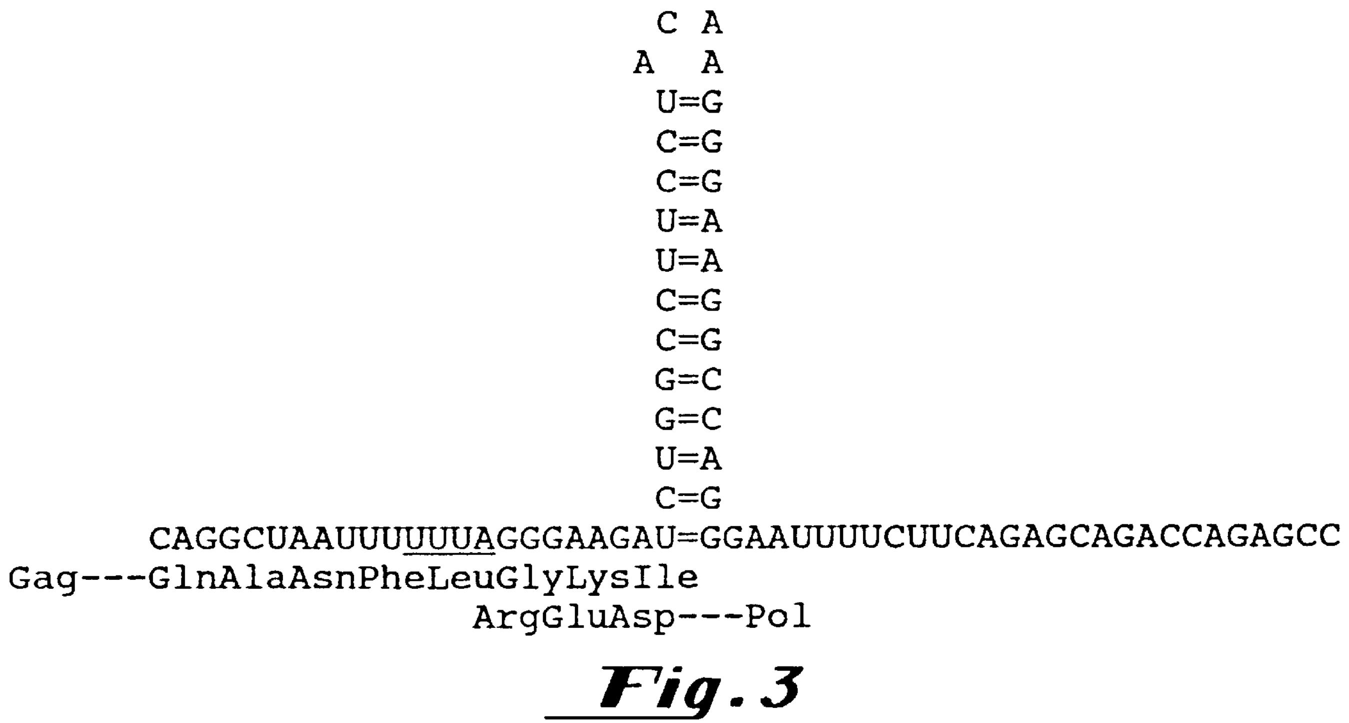
FIG. 3 is a computer-predicted secondary structure of the gag-pol frame shift region and possible mechanisms of inhibition of frame shifting.
Figure 4:
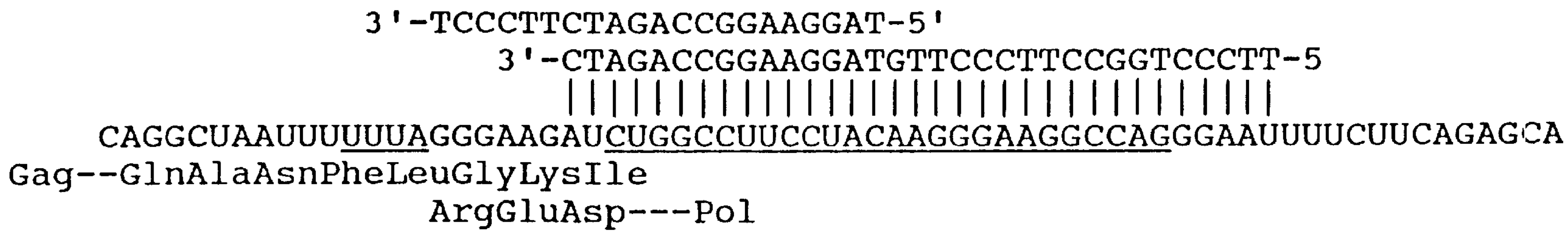
FIG. 4 depicts antisense oligonucleotide interference with gag-pol frame shifting.

In HIV and other retroviruses, near the site of frame shifting, there is a potential for the formation of significant RNA secondary structure. A computer predicted structure for HIV-1 is illustrated in FIG. 3. The potential formation of RNA secondary structures near the sites of ribosomal frame shifting exists in a number of viral gag-pol fusions. T. Jacks, K. Townsley, H. E. Varmus, J. Majors, *Proc. Natl. Acad. Sci. USA*, 84:4298 (1987); T. Jacks, M. D. Power, F. R. Masiarz, P. A. Luciw, P. J. Barr, H. E. Varmus, *Nature*, 331:280 (1988); and I. Brierley, P. Digard, S. C. Inglis, *Cell*, 57:537 (1989). It is now discovered that targeting the region between the HIV gag and pol genes with antisense oligonucleotides is effective in modulating the expression of the gag-pol fusion protein. FIG. 3 depicts the mRNA region of interest in the instant example, including the predicted stem-loop structure near the site of frameshifting and the predicted amino acid sequence of the gag and gag-pol fusion proteins near the frameshift site. FIG. 4 depicts the sequences of two representative antisense oligonucleotides which would be expected to modulate ribosomal frameshifting and translation of the target mRNA. By binding to this site by any of the following methods, it is possible to perturb the normal course of gene expression and as a result, inhibit the virus.

It is now discovered that compounds which specifically bind to the gag-pol frameshift region and interfere with translation and/or frameshifting are believed to have activity as therapeutic agents for retroviral infection. It is intended that all retroviruses which have RNA secondary structures at the gag-pol junctions fall within the spirit and scope of this invention. Different strains and types of retroviruses will have different gag-pol junctions with different secondary structures. This invention can be practiced on different strains or types of retroviruses by changing the sequence of the oligonucleotide to complement the structure of the alternative strain or type of retrovirus. Cells will be treated with the following oligonucleotides:

| Sequence 5'--3' | |
| --- | --- |
| TAGGAAGGCCAGATCTTCCCT | (SEQ ID NO: 38) |
| AAGAAAATTCCCTGGCCTTCCCTTGTAGGAAGGCCAG | (SEQ ID NO: 39) |
| TGCTCTGAAGAAAATTCCCT | (SEQ ID NO: 40) |
| TCTGAAGAAAATTCCCTGGC | (SEQ ID NO: 41) |
| GAAGAAAATTCCCTGGCCTT | (SEQ ID NO: 42) |
| CTGGCCTTCCCTTGTAGGAA | (SEQ ID NO: 43) |
| GCCTTCCCTTGTAGGAAGGC | (SEQ ID NO: 44) |

-continued

| Sequence 5'--3' | |
|---|---|
| TTCCCTTGTAGGAAGGCCAG | (SEQ ID NO: 45) |
| CCTTGTAGGAAGGCCAGATC | (SEQ ID NO: 46) |
| TGTAGGAAGGCCAGATCTTC | (SEQ ID NO: 47) |

Figure 5:
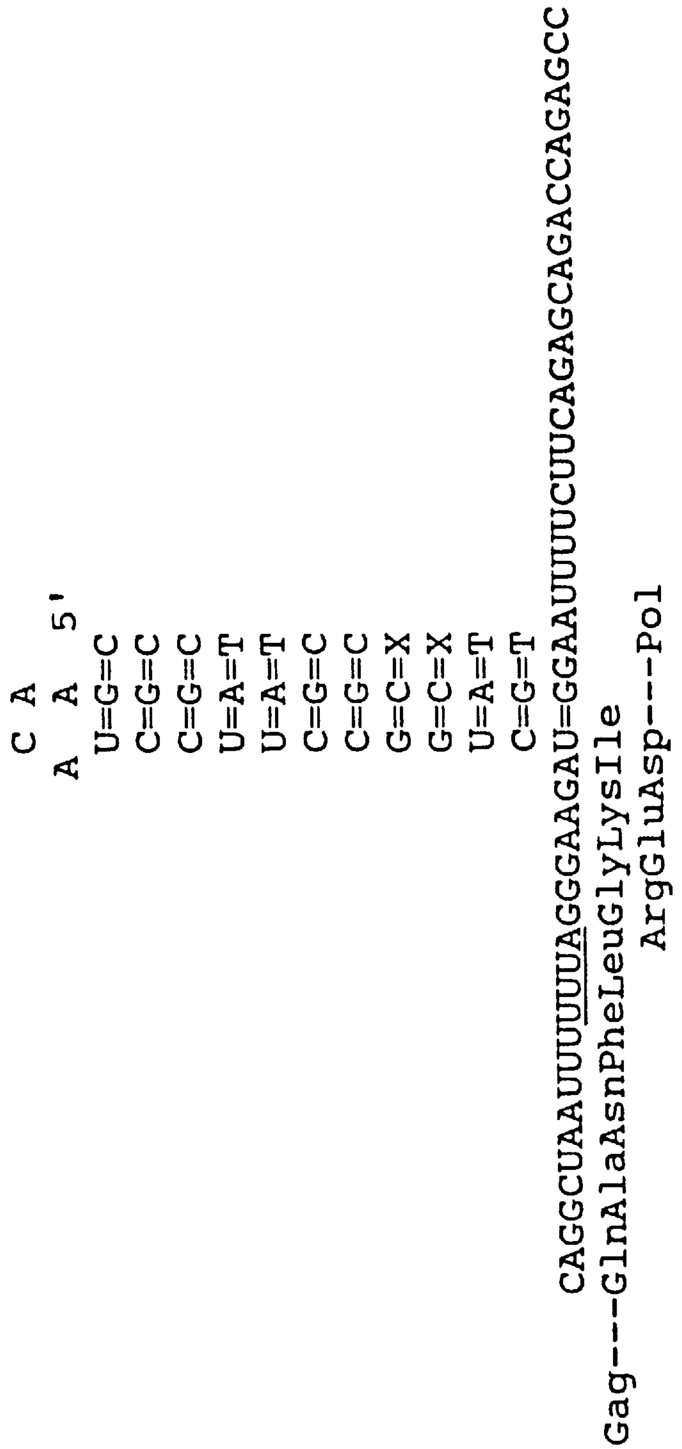
FIG. 5 shows possible interference with gag-pol frame shifting through nucleotide triplex formation.

It is also disclosed that the gag-pol RNA structure can be perturbed by binding to it by triple strand formation (see FIG. 5). In contrast to heteroduplex formation, where the RNA secondary structure is broken by an invading strand, triple strand formation generally preserves the existing RNA duplex hydrogen bonding pattern, but binds in a helical groove with additional hydrogen bonds. Oligonucleotides of the following sequence will be tested:

| Sequence 5'--3' | |
|---|---|
| CCCTTCCXXTT | (SEQ ID NO: 48) |
| CCTTCCXXT | (SEQ ID NO: 49) |
| GGGAAGGXXAG | (SEQ ID NO: 50) |
| GGAAGGXXA | (SEQ ID NO: 51) |

where X is any heterocyclic base containing a hydrogen bond acceptor. The assay for translation and ribosomal frame shifting has been previously described in T. Jacks, M. D. Power, F. R. Masiarz, P. A. Luciw, P. J. Barr, H. E. Varmus, *Nature*, 331:280 (1988). The assay will be performed as described with the addition of the above oligonucleotides.

Example 3. Synthesis of oligonucleotides:

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

Oligonucleotides having abasic linkers were synthesized using 5-branched modifier C3 amidites (Glen Research, Sterling Va.) at the abasic positions.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0. Oligodeoxynucleotides and phosphorothioates were judged from electrophoresis to be greater than 80% full length material.

RNA oligonucleotide synthesis was performed on an ABI model 380B DNA synthesizer. The standard synthesis cycle was modified by increasing the wait step after the pulse delivery of tetrazole to 900 seconds. The bases were deprotected by incubation in methanolic ammonia overnight. Following base deprotections the oligonucleotides were dried in vacuo. The t-butyldimethylsilyl protecting the 2' hydroxyl was removed by incubating the oligonucleotide in 1M tetrabutylammoniumfluoride in tetrahydrofuran overnight. The RNA oligonucleotides were further purified on $C_{18}$ Sep-Pak Cartridges (Waters, Division of Millipore Corp., Milford Mass.) and ethanol precipitated.

Example 4. Antisense targeting to the gag-pol RNA:

Two vectors for assaying frame-shift ability were constructed with the gag-pol shift site interposed between an MMTV promotor and the luciferase gene. In one case the luciferase is in frame and is expressed constitutively. In the other vector an extra base is present such that the luciferase is out of frame by one base; a frameshift at the gag-pol shift site is necessary to get luciferase expression. In vitro translation of this mRNA shows that the constitutive (in-frame) vector expresses twenty times as much luciferase as does the out-of frame vector.

Oligonucleotides were designed to be complementary to the gag-pol shift site or the adjacent hairpin structure shown in FIG. 3. These oligonucleotides are listed in Table 1:

TABLE 1

Oligonucleotides Complementary to the gag-pol Shift Region

| ISIS# | Code | Sequence | Modification | SEQ. ID.NO. |
|---|---|---|---|---|
| 3332 | GP1 | CCU UCC CUU GTA | 2'-O-Methyl | 1 |
| 3336 | GP5 | AGA AAA UUC CCU G | 2'-O-Methyl | 2 |
| 3337 | GP6 | CCA GAU CUU CCC U | 2'-O-Methyl | 3 |

TABLE 1-continued

Oligonucleotides Complementary to the gag-pol Shift Region

| ISIS# | Code | Sequence | Modification | SEQ. ID.NO. |
|---|---|---|---|---|
| 3338 | GP7 | AUC UUC CC | 2'-O-Methyl | 4 |
| 3339 | GP8 | UCU UCC CU | 2'-O-Methyl | 5 |
| 3414 | | CAT GGT CCT CCT ACA CGG TC | DNA | 6 |
| 3561 | | CAU CCU CCU CCU AGA GGG UC | 2'-O-Methyl | 7 |
| 3746 | | GAA AAU UCC UUU AUC UUC CC | 2'-O-Methyl | 8 |
| 3747 | | AGA AAA TTT CNN NTC TTC CCT AA | N = abasic linker | 9 |
| 3748 | | AGA AAA TTT CNN NNN TCT TCC CTA A | " | 10 |

These oligonucleotides were tested for their ability to inhibit in vitro translation of gag-pol mRNA. The oligonucleotide was incubated with gag-pol mRNA for 5 minutes at 65° C., and 30 minutes at 37° C. in phosphate buffer. Reticulocyte lysate and 20 amino acids were added according to kit instructions (Promega, Madison, Wis.) and incubated for one hour. Luciferase assay buffer and ATP were added, and luciferase activity was measured using a luminometer.

Figure 6A:
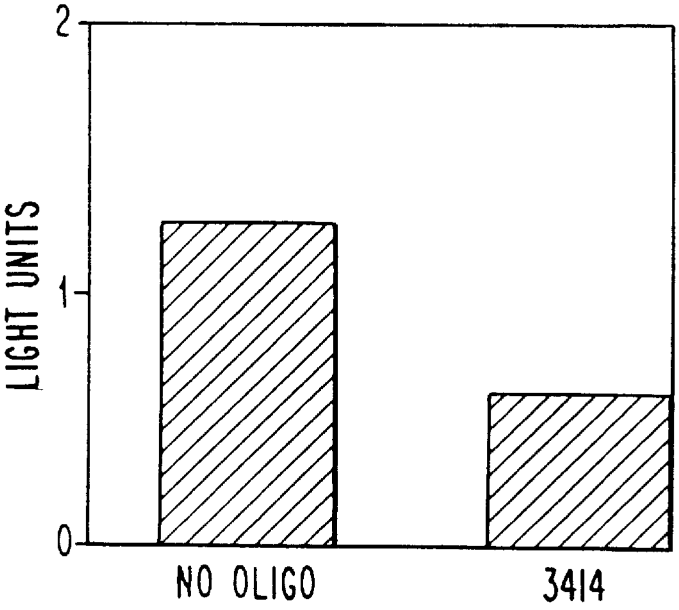
FIGS. 6A and 6B are a graphic representation showing inhibition of gag-pol expression by ISIS 3414 and ISIS 3561.
Figure 6B:
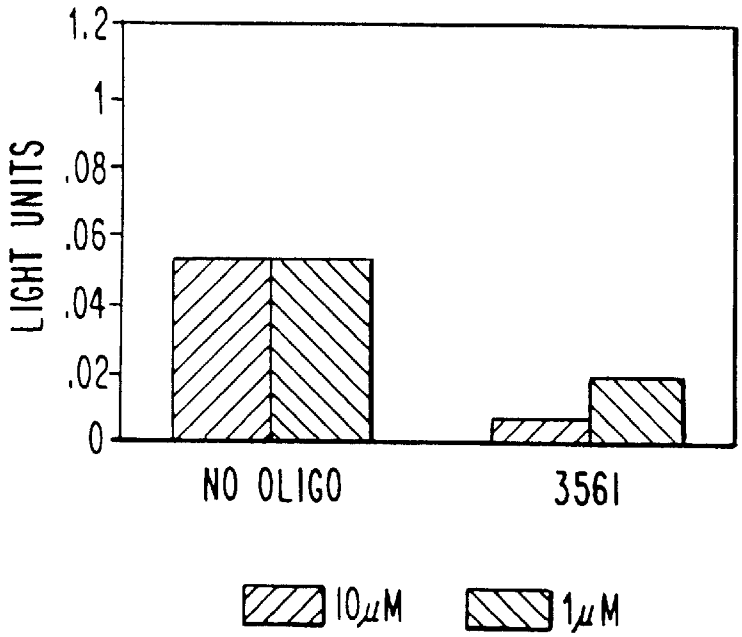

Translation of the gag-pol mRNA was inhibited by approximately 50% with ISIS 3414, a DNA oligonucleotide 20 bases in length. When the same sequence was used as a 2'-O-methyl oligonucleotide (ISIS 3561), approximately 90% inhibition was achieved (10 $\mu$M oligonucleotide in both cases). This is shown in FIG. 6.

Additional oligonucleotides, also shown in Table 1, were designed to hybridize to and disrupt the stem-loop structure believed to be present at the gag-pol shift site. ISIS 3746 is complementary to the region immediately downstream of the shift site (just upstream of the stem-loop). ISIS 3747 and 3748 are complementary to the regions both upstream and downstream of the stem-loop. These oligonucleotides have a "bridge" region connecting their two domains; the bridge is 3 bases long (UUU) in ISIS 3746, which is a 2-O-methyl. The bridge region is an abasic linker 3 subunits long in the case of ISIS 3747, and 5 subunits long in ISIS 3748.

Figure 7A:
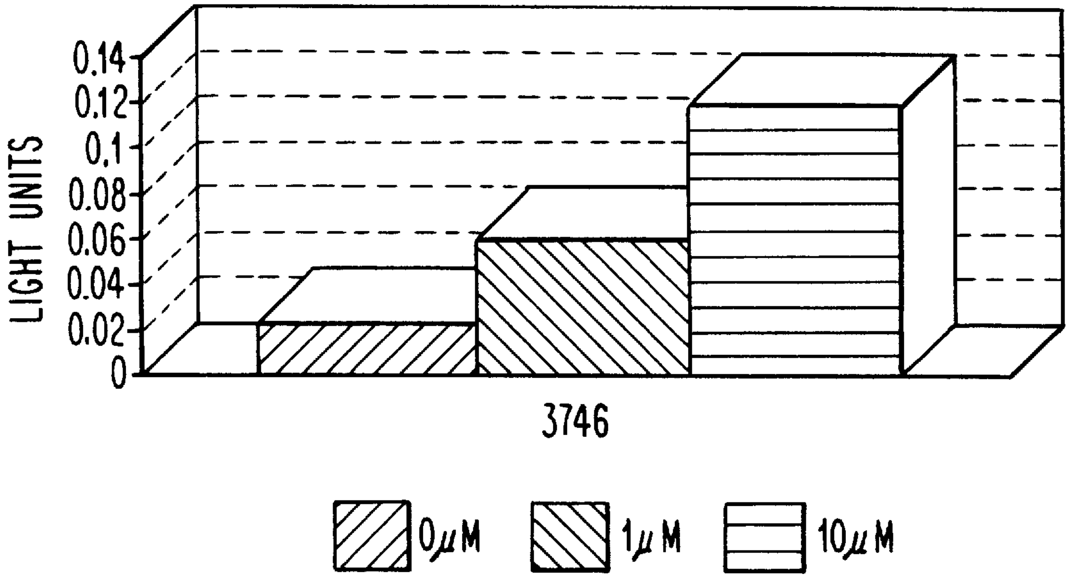
FIG. 7 is a graphic depiction of modulation of gag-pol expression by antisense oligonucleotides ISIS 3746, 3747 and 3848.
Figure 7B:
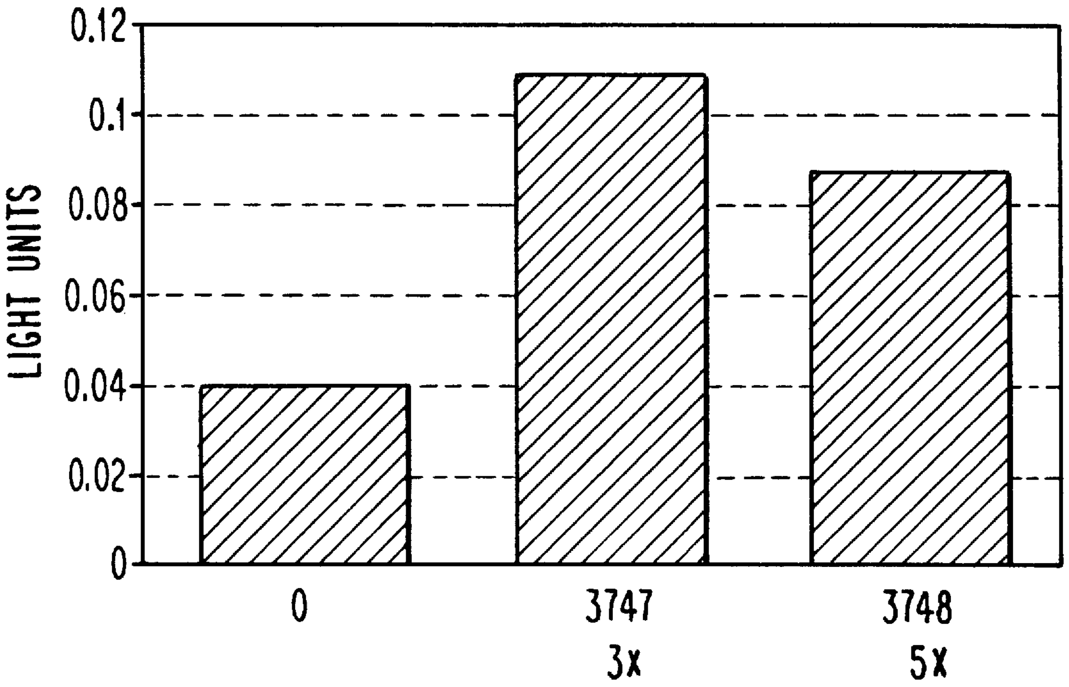

Using the gag-pol luciferase in vitro translation assay of Example 4, ISIS 3746, 3747 and 3748 were shown to modulate the expression of the gag-pol gene, with a net increase in gag-pol expression. This modulation is shown in FIG. 7.

Example 5. Interference with gag-pol frameshifting through triplex interactions:

A series of oligonucleotides complementary to the hairpin region at the gag-pol shift site were synthesized. These oligonucleotides are shown in Table 2:

TABLE 2

Oligonucleotides for Triplex Formation at the gag-pol Shift Site

| ISIS# | Sequence | | SEQ. ID.NO. |
|---|---|---|---|
| 3718 | CCC UUC CAN UC | (N = mixture of A, G, C, U) | 11 |
| 3719 | CCC UUC CGN UC | " | 12 |
| 3720 | CCC UUC CCN UC | " | 13 |
| 3721 | CCC UUC CUN UC | " | 14 |
| 4007 | CCC UUC CCA UC | | 15 |
| 4008 | CCC UUC CCC UC | | 16 |

TABLE 2-continued

Oligonucleotides for Triplex Formation at the gag-pol Shift Site

| ISIS# | Sequence | SEQ. ID.NO. |
|---|---|---|
| 4009 | CCC UUC CCC UC | 17 |
| 4010 | CCC UUC CCU UC | 18 |

Triplex formation upon addition of oligonucleotides was assayed by gel assay. gag-pol mRNA was incubated overnight with oligonucleotide at 22° C. in 100 mM NaCl, 25 mM TrisOAc, pH 5, 2 mM MgCl2 and 1 mM spermidine. Triplexes were resolved from duplexes by electrophoresis on a 15% acrylamide gel in the presence of 50 mM NaCl and 2 mM MgC12.

Figure 8:
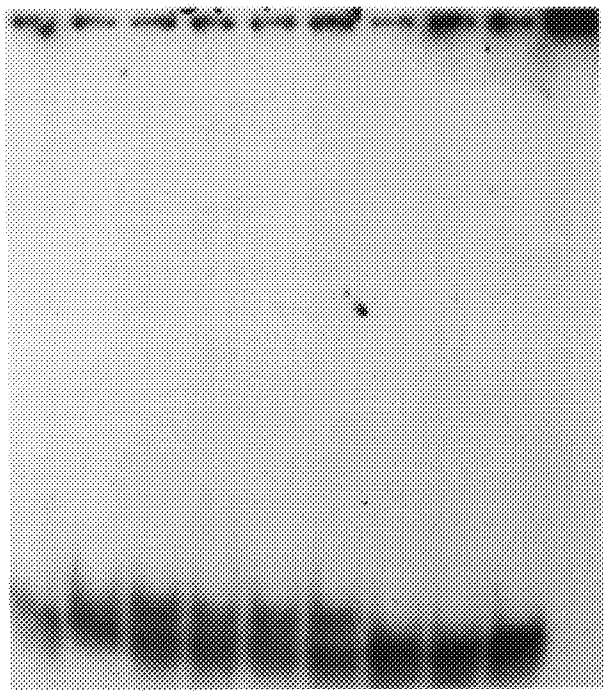
FIG. 8 is a polyacrylamide gel depicting the results of a triplex formation assay using gag-pol mRNA and oligonucleotides ISIS 4007, ISIS 4008, ISIS 4009 and ISIS 4010.

ISIS 3720 was found to form a triplex with the gag-pol mRNA. When the "N" position of this oligo is replaced by A,G,C, or U, the oligonucleotides containing A or G in place of N (ISIS 4007 and 4008) were found to be the even better triplex formers than ISIS 3720. This is shown in FIG. 8.

Additional oligonucleotides have been synthesized having the sequences CCC UUC CNN UCU AUC UUC CC (SEQ. ID. NO. 23) and CCC UUC CNN UCA UCU UCC C (SEQ. ID. NO. 24). These oligonucleotides are designed to form a triplex with the gag-pol hairpin loop, and also have a region which is designed to Watson-Crick pair with the single-stranded region at the base of the hairpin.

Example 6. Antisense oligonucleotides to the CAR element:

A series of oligonucleotides to the CAR element was prepared. These oligonucleotides, shown in Table 3, will be assayed for ability to modulate the function of the CAR element.

TABLE 3

Antisense Oligonucleotides to the HIV CAR Element

| Oligo # | Sequence | Modification | SEQ. ID.NO. |
|---|---|---|---|
| 4080 | GCC CAT AGT GCT TCC TG | 2'-O-Methyl | 19 |
| 4086 | " | 2'-O-Methyl P = S | |
| 4081 | TCA TTG ACG CTG CGC CC | 2'-O-Methyl | 20 |
| 4087 | " | 2'-O-Methyl P = S | |
| 4082 | TAC CCT CAG CGT CAT TG | 2'-O-Methyl | 21 |
| 4088 | " | 2'-O-Methyl P = S | |
| 4083 | TGT CTG GCC TGT ACC GT | 2'-O-Methyl | 22 |
| 4089 | " | 2'-O-Methyl P = S | |

What is claimed is:

1. An oligonucleotide having 6 to 50 bases which binds to at least a portion of the gag-pol region of HIV RNA having secondary structure, said oligonucleotide modulating HIV gag-pol gene expression.

2. The oligonucleotide of claim 1 comprising SEQ. ID. NO. 6, SEQ. ID. NO. 7, SEQ. ID. NO. 8, SEQ. ID. NO. 9 or SEQ. ID. NO. 10.

3. The oligonucleotide of claim 1 comprising the sequence CCC UUC CNN UC (nucleotides 1–11 of SEQ ID NO:23).

4. The oligonucleotide of claim 1 comprising SEQ. ID. NO. 11, SEQ. ID. NO. 12, SEQ. ID. NO. 13, SEQ. ID. NO. 14, SEQ. ID. NO. 15, SEQ. ID. NO. 16, SEQ. ID. NO. 17 or SEQ. ID. NO. 18.

5. The oligonucleotide of claim 1 comprising SEQ. ID. NO. 23 or SEQ. ID. NO. 24.

6. The oligonucleotide of claim 1 which forms a duplex structure with said region wherein formation of said duplex structure modulates HIV gag-pol gene expression.

7. The oligonucleotide of claim 1 which forms a triplex structure with said region wherin formation of said triplex structure modulates HIV gag-pol gene expression.

* * * * *

UNITED STATES PATENT AND TRADEMARK OFFICE

CERTIFICATE OF CORRECTION

PATENT NO. : 5,866,698

DATED : February 2, 1999

INVENTOR(S) : Ecker et al.

It is certified that error appears in the above-indentified patent and that said Letters Patent is hereby corrected as shown below:

Col. 15, Table 1, ISIS# 3561, SEQ.ID. NO. 7, please delete "CAU CCU CCU CCU AGA GGG UC" and insert therefor --CAU GGU CCU CCU ACA GGG UC--.

At col. 16, Table 3, Oligo# 4082, SEQ. ID. NO.21, please delete "TAC CCT CAG CGT CAT TG" and insert therefor --TAC CGT CAG CGT CAT TG--.

Signed and Sealed this

Eighteenth Day of April, 2000

Attest:

Q. TODD DICKINSON

Attesting Officer

*Director of Patents and Trademarks*